[19] United States Patent
Tobkes et al.

[11] 4,196,198
[45] Apr. 1, 1980

[54] ANTIBIOTIC BM123-ALKYL SULFATE COMPLEXES

[75] Inventors: Martin Tobkes, Spring Valley; Murray Dann, Pearl River, both of N.Y.

[73] Assignee: American Cyanamid Company, Stamford, Conn.

[21] Appl. No.: 874,306

[22] Filed: Feb. 2, 1978

[51] Int. Cl.$^2$ .................. A61K 31/70; A61K 31/71
[52] U.S. Cl. .................................. 424/180; 424/181; 536/17 R
[58] Field of Search .................. 536/17; 424/181, 180

[56] References Cited
U.S. PATENT DOCUMENTS 4,007,167  2/1977  Mautin et al. .................. 536/17

Primary Examiner—Jerome D. Goldberg
Attorney, Agent, or Firm—Edward A. Conroy, Jr.

[57] ABSTRACT

This disclosure describes reversible complexes of antibiotic trans-BM123γ with an alkali metal alkyl sulfate and a process for preparing same. The complexes are useful as animal feed supplements which significantly enhance the growth rate of animals and poultry.

13 Claims, No Drawings

ANTIBIOTIC BM123-ALKYL SULFATE COMPLEXES

BRIEF SUMMARY OF THE INVENTION

This invention relates to a method of recovering antibiotic trans-BM123γ from fermentation whole harvest mashes containing it. More particularly, the process involves adding an alkali metal alkyl sulfate (or mixtures thereof) either to the whole harvest mash or to the filtered fermentation liquor, and recovering the so precipitated antibiotic-alkyl sulfate reversible complex (or mixture of complexes) by any convenient means. The invention also relates to the use of the so prepared complexes in animal feed supplement compositions for enhancing the growth rate of animals such as poultry, swine, early weaned pigs, and ruminants such as cattle, sheep and goats.

DETAILED DESCRIPTION OF THE INVENTION

Antibiotic trans-BM123γ is formed by fermentative biosynthesis during the cultivation under controlled conditions of new strains of an undetermined species of Nocardia NRRL 5646, NRRL 8050, NRRL 11230 and mutants thereof. The preparation and properties of antiobiotics trans-BM123γ$_1$, trans-BM123γ$_2$, and trans-BM123γ are set forth in U.S. Pat. No. 4,007,167 which is hereby incorporated by reference. Hereinafter, trans-BM123γ refers to a mixture in any proportions of trans-BM123γ$_1$ and trans-BM123γ$_2$. The problem of recovering the antibiotic economically has been a serious one. In the patent referred to above, adsorption on carbon followed by elution and column chromatography are employed. Such a process is not excessively expensive when pure antibiotic is required for medical usage. However, when the antibiotic is to be used in animal feed supplement compositions the factor of cost is a very serious matter and there is therefore, a need for an inexpensive process of recovering the antibiotic for this purpose.

The present invention deals with a process and in a more specific aspect also with a product. The process involves the precipitation of the antibiotic either from the whole harvest mash or from the filtered fermentation broth by the addition of alkali metal alkyl sulfates. The alkali metal alkyl sulfates operable in the novel process of the present invention may be represented by the following general formula:

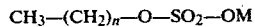

$$CH_3-(CH_2)_n-O-SO_2-OM$$

wherein n is an integer from 9 to 17, inclusive, and M is sodium or potassium. Typical such alkali metal alkyl sulfates which may be employed are, for example, sodium decyl sulfate, potassium hendecyl sulfate, sodium lauryl sulfate, potassium tridecyl sulfate, sodium myristyl sulfate, potassium pentadecyl sulfate, sodium cetyl sulfate, potassium heptadecyl sulfate, and sodium octadecyl sulfate. Mixtures of alkali metal alkyl sulfates may also be employed such as a mixture of sodium hendecyl sulfate and potassium octadecyl sulfate; a mixture of potassium decyl sulfate and sodium heptadecyl sulfate; a mixture of potassium lauryl sulfate and potassium cetyl sulfate; a mixture of sodium tridecyl sulfate, potassium myristyl sulfate, and sodium pentadecyl sulfate, and the like. When mixtures of alkali metal alkyl sulfates are employed, then a corresponding mixture of antibiotic-alkyl sulfate complexes are obtained.

The novel process of the present invention provides almost complete removal of the antibiotic activity from the fermentation mash or broth. Furthermore, the antibiotic-alkyl sulfate complex so obtained can be used without separation of the constituents in animal feed supplement compositions, which is an important economic advantage. Therefore, in one of the aspects of the present invention the complex of antibiotic trans-BM123γ and an alkali metal alkyl sulfate is included as a product.

The product of the antibiotic and alkali metal alkyl sulfate has been referred to as a reversible antibiotic-alkyl sulfate complex. Its exact chemical nature has not been determined, but covalent bonding is not involved and the product is not a physical mixture. This complex, derived from the interaction of the antibiotic and an alkali metal alkyl sulfate, is not necessarily combined in any limiting stoichiometry. The chemical bonds are reversible since the antibiotic trans-BM123γ may be recovered from the complex by various means such as adsorption on a cross-linked carboxymethyldextran gel column followed by elution with aqueous acid. While it is not intended to limit the present invention to theories of chemical constitution and the like, it seems probable that the complex of the present invention is sufficiently reversible so that under conditions of use in animal feed supplement compositions the antibiotic is set free upon ingestion.

As starting material for the novel process of the present invention there may be employed the whole harvest mash obtained after completion of a fermentation with Nocardia sp. NRRL 5646, NRRL 8050, NRRL 11230 or mutants thereof. Preferably, there is employed the fermentation liquor or broth which has been clarified by removing the mycelia and other insolubles by filtration. Diatomaceous earth or any other conventional filtration aid may be used to assist in the filtration. In either case, the pH of the whole mash or of the filtered broth is first adjusted to between 1.9 and 5.0, preferably 2.0–2.5, with an acid. Suitable acids for this purpose may be, for example, hydrochloric acid, sulfuric acid, trifluoroacetic acid, and the like, although even glacial acetic acid may be used. Then, an aqueous solution of an alkali metal alkyl sulfate (or a mixture of alkali metal alkyl sulfates) is added slowly, with stirring, at ambient temperatures. The entire process of the present invention is preferably carried out at from about 15° C. to about 30° C., conveniently at room temperature. The antibiotic and alkyl sulfate form a complex which is water insoluble and thus precipitates. The precipitated complex or, in the case of the whole mash, the precipitated complex together with the fermentation mash solids, is then removed by filtration or centrifugation and dried. The products so obtained may be dried by (1) slurrying the wet solids in polar, water miscible non-solvents such as acetone followed by filtration, rinsing and air-drying; or by (2) reslurrying the wet solids in water and freeze drying or spray drying.

When the products of the present invention are thus carefully dried under temperature conditions which do not degrade antibiotic trans-BM123γ, they are usually white to tan powders in the case of the alkyl sulfate complex. In the case of the alkyl sulfate complex associated with dried harvest mash solids, they are usually gray to brown powders or solids. In the dry form, these products are extremely stable, keeping without significant loss of antibiotic activity for considerable periods of time. This long storage life is, of course, an important practical advantage.

It is an advantage of the present invention that the amount of alkali metal alkyl sulfate added to precipitate the complex with the antibiotic is not particularly critical and no exact stoichiometric relations need be followed. The trans-BM123γ content of the whole mash may be readily determined by microbiological assay as set forth in U.S. Pat. No. 4,007,167. The preferred method is an adaptation of the *Staphylococcus aureus* turbidimetric assay for tetracycline that is described in "Assay Methods of Antibiotics, a Laboratory Manual" by Grove & Randall, Medical Encyclopedia, Inc. (1955), pages 48–52, substituting *Klebsiella pneumoniae* as the test organism. The required amount of alkali metal alkyl sulfate is then preferably dissolved or suspended in a convenient quantity of water and the aqueous solution or suspension is added to the whole mash as described above. Any excess alkali metal alkyl sulfate present will merely remain in solution upon filtration.

In general, the amount of alkali metal alkyl sulfate required to precipitate antibiotic trans-BM123γ from a clarified liquor is about one gram per gram of trans-BM123γ activity in the clarified liquor. The higher level of alkali metal alkyl sulfate required to precipitate trans-BM123γ from whole mash than from clarified liquor is due to coprecipitation of other basic material present in the whole mash. Conveniently, the minimum amount of alkali metal alkyl sulfate required to form the complex with the antibiotic in the clarified liquor from any particular fermentation batch may be readily determined as follows. A sample (conveniently 50–100 ml.) of the fermentation whole harvest mash is taken and clarified by removing the mycelia and other insolubles by filtration, preferably with a filter aid. The filtrate is then acidified to a pH of 1.9–2.5 with dilute aqueous mineral acid such as dilute hydrochloric acid, dilute sulfuric acid, dilute phosphoric acid, or the like. This solution is then titrated with the particular aqueous solution of alkali metal alkyl sulfate which is to be used until no further precipitate or turbidity forms. The amount of alkali metal alkyl sulfate solution for the clarified liquor of the fermentation batch is then calculated from the titer of the sample taken, providing also for a slight excess.

This invention also relates to animal feed supplement compositions effective in accelerating the growth rate of animals and poultry. In recent years the use of antibiotics in animal feeds for improving growth characteristics and efficiency of feed utilization has become of considerable economic importance. In accordance with the present invention, the dried alkyl sulfate complex or the dried harvest mash solids containing the alkyl sulfate complex, either alone or in combination with suitable carriers, when added to an animal feed, aid in increasing the growth rate. In addition, feed efficiency is improved. The present invention has the advantage that the growth rate of non-ruminants such as poultry and swine and especially weanling pigs is significantly increased, and that feed conversion rates are noticeably enhanced.

The feed supplement compositions of the present invention are administered in an amount sufficient to furnish approximately the following dosage levels in mg./head/day:

Large ruminants: 350
Small Ruminants: 200
Non-ruminants: 100
Poultry: 2

The milligrams per pound of antibiotic trans-BM123γ present in any particular supplement composition of the present invention may be readily determined by bioassay as set forth in U.S. Pat. No. 4,007,167. From the potency data thus obtained, the pounds of feed supplement composition to be used per ton of feed may be readily calculated. A wide variety of carriers may be used in the preparation of the feed supplement compositions of this invention containing the dried alkyl sulfate complex or the dried harvest mash solids containing the alkyl sulfate complex. Carriers suitable for use to make up the feed supplement compositions include the following: soybean meal, alfalfa meal, cotton seed oil meal, linseed oil meal, cornmeal, cane molasses, urea, bone meal, corncob meal, and the like. The carrier promotes a uniform distribution of the complex in the finished feed into which the supplement is blended. It thus performs an important function by ensuring proper distribution of the complex throughout the feed.

For a clearer understanding of the invention, specific examples of it are set forth below. These examples are merely illustrative, and are not to be understood as limiting the scope and underlying principles of the invention in any way.

EXAMPLE 1

Preparation of antibiotic BM123γ-lauryl sulfate complex from whole harvest mash

A 28 liter portion of Nocardia sp. NRRL 11230 fermentation mash containing 571 mcg. of antibiotic BM123γ per ml. is adjusted to pH 2.0 with dilute sulfuric acid. A 218 g. portion of sodium lauryl sulfate is added as a 5% aqueous solution and the pH is readjusted to 2.0 with dilute sulfuric acid. The mixture is stirred for 45 minutes, 60 g. of diatomaceous earth is added, and the mixture is filtered. The solid complex is dried in vacuo at 40° C. for 67 hours giving 1.4 kg. of material containing the antibiotic BM123γ-lauryl sulfate complex.

Nocardia sp. NRRL 11230 has cultural, physiological, and morphological characteristics essentially the same as those of NRRL 5646 and NRRL 8050.

EXAMPLE 2

Preparation of antibiotic BM123γ-lauryl sulfate complex from harvest mash filtrate To 6 liters of Nocardia sp. NRRL 11230 fermentation mash filtrate containing 447 mcg. of antibiotic BM123γ per ml. there is added with stirring 90.0 g. of diatomaceous earth followed by 420 ml. of 10% w/v aqueous sodium lauryl sulfate. The pH of the suspension is adjusted to 2.5 with 50% w/w sulfuric acid, stirred for 15 minutes and then filtered. The filter cake is rinsed with a small amount of water and then dried for three days in vacuo without heat, giving 223.4 g. of product assaying 4.9 mcg./mg.

EXAMPLE 3

Growth promoting effect of antibiotic BM123γ-alkyl sulfate complex on poultry

One day old Hubbard X Hubbard crossbred chicks are used. These chicks are randomly allotted to pens of ten chicks (5 male and 5 female) each. Four experiments are started at one week intervals. In each experiment, four pens of chicks are used for unmedicated controls and two pens of chicks are used at each level of drug. Thus a total of 16 pens (160 chicks) are used as controls and a total of 8 pens (80 chicks) are used at each dose level for each drug. The duration of the experiment is 14 days.

The controls are offered an unmedicated diet of broiler ration (composition follows) and water ad libitum. The medicated chicks are offered the same diet containing either antibiotic BM123γ-lauryl sulfate complex precipitated from crude fermentation mash or antibiotic BM123γ-lauryl sulfate complex precipitated from fermentation mash filtrate at levels of 5, 10 and 20 parts per million, and water ad libitum. The weight of the chicks is determined at the beginning and on completion of the experiments. Weight gain and the amount of feed consumed are also determined. The data are averaged and summarized in Table I below, together with the percent improvement in weight gains and feed/gain ratios.

| -continued | |
|---|---|
| Folic acid (10%) | 13.0 |
| Choline Chloride (50%) | 908.0 |
| Vitamin $B_{12}$ (20 mg./lb.) | 227.0 |
| Corn oil | 50.0 |
| Fine ground corn | 2,582.4 |

TABLE I

| Treatment | Drug Level In Feed (ppm) | Ave. Weight Per Chick in Grams | | Av. Weight Gain Per Chick In Grams | Feed Consumed Per Chick In Grams (Average) | Feed/Gain Ratio | % Improvement In | |
|---|---|---|---|---|---|---|---|---|
| | | Start | End | | | | Gain | Feed/Gain Ratio |
| Control | | 41.3 | 284.1 | 242.8 | 338.0 | 1.392 | | |
| Antibiotic BM123γ-lauryl sulfate complex precipitated from crude fermentation mash | 5 | 41.3 | 285.0 | 243.7 | 332.7 | 1.365 | 3.7 | 1.9 |
| | 10 | 41.3 | 295.1 | 253.8 | 344.4 | 1.357 | 5.0 | 2.5 |
| | 20 | 41.3 | 302.4 | 261.1 | 339.4 | 1.300 | 5.8 | 6.6 |
| Antibiotic BM123γ-lauryl sulfate complex precipitated from fermentation mash filtrate | 5 | 41.3 | 291.7 | 250.4 | 344.3 | 1.375 | 3.1 | 1.2 |
| | 10 | 41.3 | 295.6 | 254.3 | 343.3 | 1.350 | 4.7 | 3.0 |
| | 20 | 41.3 | 301.3 | 260.0 | 347.9 | 1.338 | 7.1 | 3.9 |

| Broiler ration formula | |
|---|---|
| Component | Percent by weight |
| Ground yellow corn | 53.45 |
| Soybean oil meal (49%) | 28.00 |
| Menhaden fish meal (60%) | 5.00 |
| Corn gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |

*Trace mineral mixture

| Component | | One lb./ton furnishes |
|---|---|---|
| Manganese | 12.50% | 62.5 ppm |
| Iron | 6.00% | 30.0 ppm |
| Zinc | 5.00% | 25.0 ppm |
| Copper | 0.65% | 3.25 ppm |
| Iodine | 0.35% | 1.75 ppm |
| Cobalt | 0.25% | 1.25 ppm |
| Calcium (min. 15.30%, max. 18.35%) | | |

**Vitamin premix for one ton

| Component | Weight in grams |
|---|---|
| DL. Methionine | 453.6 |
| Butylated hydroxy toluene | 113.6 |
| Vitamin A (30,000 mcg./g.) | 100.0 |
| Vitamin $D_3$ (200,000 mcg./g.) | 5.0 |
| Vitamin E (20,000 mcg./lb.) | 45.4 |
| Riboflavin | 4.0 |
| Niacinamide | 25.0 |
| Calcium pantothenate | 8.0 |
| Vitamin K (menadione | 1.0 |

EXAMPLE 4

Growth promoting effect of antibiotic BM123γ-alkyl sulfate complex on weanling pigs Forty, five year old weanling pigs are allotted randomly into four groups of ten pigs each. One group serves as unmedicated controls. The other three groups receive antibiotic BM123γ-lauryl sulfate complex in their diets at levels of 25, 50 and 100 ppm. Control animals are offered a modified pig starter ration (composition follows) and water ad libitum. The other groups receive the same diet except that it contains the aforementioned complex at the levels indicated.

The weight of the pigs is determined at the start of the experiment and two weeks later. Average daily weight gains, average overall weight gains, weight of food consumed per pen, feed/gain ratios and the percent improvements of weight gains and feed/grain ratios over controls are also determined and appear in Table II below.

| Modified pig starter ration | |
|---|---|
| Composition | lb./ton |
| Corn | 1250 |
| Farm blend protein supplement* | 600 |
| Dried whey | 150 |

*Farm blend protein supplement

Processed grain by-products, animal protein products, plant protein products, cane molasses, forage products, vitamin A supplement, D activated animal sterol, vitamin $B_{12}$ supplement, vitamin E supplement, riboflavin supplement, methionine hydroxy analog calcium, niacin, biotin, choline chloride, calcium pantothenate, defluorinated phosphate, calcium carbonate, iodized salt, sodium selenide, iron carbonate, iron sulfate, manganous oxide, copper sulfate, cobalt carbonate, zinc oxide.

| Analysis | | |
|---|---|---|
| Crude protein | ≧ | 36.0% |
| Crude Fat | ≧ | 0.5% |

| Analysis | | |
|---|---|---|
| Crude fiber | ≦ | 7.0% |
| Calcium | ≧ | 3.2% |
| Calcium | ≦ | 4.2% |
| Phosphorus | ≧ | 1.7% |
| Iodine | ≧ | 0.0003% |
| Sodium chloride | ≧ | 2.3% |
| Sodium chloride | ≦ | 3.3% |

TABLE II

| Treatment | Drug Level In Diet (ppm) | Av. Weight Per Pig In kg. Start | Av. Weight Per Pig In kg. Finish | Av. Weight Gain Per Pig in kg. 2 Weeks | Av. Weight Gain Per Pig in kg. Daily | % Improvement Over Control | Total Feed Per Pen In kg. | Feed/Gain Ratio | % Improvement Over Control |
|---|---|---|---|---|---|---|---|---|---|
| Control | | 8.45 | 13.55 | 5.13 | 0.366 | | 95.2 | 1.855 | |
| Antibiotic | 25 | 8.31 | 14.95 | 6.66 | 0.476 | 30 | 114.8 | 1.768 | 5 |
| BM123γ- | 50 | 8.15 | 14.70 | 6.57 | 0.469 | 28 | 103.3 | 1.572 | 15 |
| lauryl sulfate complex | 100 | 8.52 | 15.80 | 7.3 | 0.521 | 42 | 117.8 | 1.613 | 13 |

We claim:

1. A process of recovering an antibiotic trans-BM123γ-alkyl sulfate complex from a fermentation whole harvest mash containing antibiotic trans-BM123γ which comprises the steps of:
   (a) producing a fermentation liquor by clarifying the whole harvest mash;
   (b) acidifying the fermentation liquor to a pH of from 1.9 to 5.0;
   (c) adding to the acidified liquor, in amount sufficient to produce a complex with the antibiotic trans-BM123γ, a complexing agent selected from the group consisting of compounds of the formula:

$$CH_3-(CH_2)_n-O-SO_2-OM$$

wherein n is an integer from 9 to 17, inclusive, and M is sodium or potassium, and mixtures thereof;
   (d) removing the precipitated antibiotic trans-BM123γ-alkyl sulfate complex; and
   (e) drying the antibiotic trans-BM123γ-alkyl sulfate complex.

2. A process as defined in claim 1 wherein the complexing agent is sodium decyl sulfate.

3. A process as defined in claim 1 wherein the complexing agent is sodium lauryl sulfate.

4. A process as defined in claim 1 wherein the complexing agent is a mixture of sodium cetyl sulfate and sodium oleyl sulfate.

5. A dry complex of an alkali metal alkyl sulfate with antibiotic trans-BM123γ prepared as defined in the process of claim 1.

6. A process for the production of a dried fermentation harvest mash solids animal feed supplement containing an antibiotic trans-BM123γ-alkyl sulfate complex which comprises the steps of:

(a) acidifying a fermentation whole harvest mash containing antibiotic trans-BM123γ to a pH of from 1.9 to 5.0;
   (b) adding to the acidified mash, in amount sufficient to produce a complex with the antibiotic trans-BM123γ, a complexing agent selected from the group consisting of compounds of the formula:

$$CH_3-(CH_2)_n-O-SO_2-OM$$

wherein n is an integer from 9 to 17, inclusive, and M is sodium or potassium, and mixtures thereof;
   (c) removing the harvest mash solids together with the precipitated antibiotic trans-BM123γ-alkyl sulfate complex; and
   (d) drying the mixture of mash solids and antibiotic trans-BM123γ-alkyl sulfate complex.

7. A process as defined in claim 6 wherein the complexing agent is sodium decyl sulfate.

8. A process as defined in claim 6 wherein the complexing agent is sodium lauryl sulfate.

9. A process as defined in claim 6 wherein the complexing agent is a mixture of sodium cetyl sulfate and sodium oleyl sulfate.

10. An animal feed supplement comprising an effective amount of a dried mixture of fermentation harvest mash solids and antibiotic trans-BM12γ-alkyl sulfate complex prepared as defined in the process of claim 6.

11. An animal feed composition for improving feed efficiency and enhancing the growth rate of animals and poultry comprising a nutritionally balanced animal feed containing from about 0.0001% to about 1.0% by weight of the feed of an antibiotic trans-BM123γ-alkyl sulfate complex prepared as defined in the process of claim 1.

12. An animal feed composition for improving feed efficiency and enhancing the growth rate of animals and poultry comprising a nutritionally balanced animal feed containing from about 0.0001% to about 1.0% by weight of the feed of an animal feed supplement prepared as defined in the process of claim 6.

13. An animal feed premix for improving feed efficiency and enhancing the growth rate of animals and poultry comprising from about 70% to about 99% by weight of an edible carrier and from about 1% to about 30% by weight of an antibacterial ingredient selected from the group consisting of a dry complex as defined in claim 5, an animal feed supplement as defined in claim 10, and mixtures thereof in any proportion.

* * * * *